(12) United States Patent
Witztum et al.

(10) Patent No.: US 6,225,070 B1
(45) Date of Patent: *May 1, 2001

(54) ANTIBODIES TO OXIDATION-SPECIFIC EPITOPES ON LIPOPROTEIN AND METHODS FOR THEIR USE IN DETECTING, MONITORING AND INHIBITING THE GROWTH OF ATHEROMA

(75) Inventors: Joseph L. Witztum; Wulf Palinski; Sohvi Hörkkö, all of San Diego; Daniel Steinberg, La Jolla, all of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/908,746

(22) Filed: Aug. 7, 1997

(51) Int. Cl.$^7$ .................. G01N 435/71; G01N 435/794; A61K 424/1301

(52) U.S. Cl. ...................... 435/7.1; 435/7.94; 435/11; 424/130.1; 424/7.4; 530/387.1

(58) Field of Search ............................... 435/7.1, 11, 7.94; 424/130.1, 7.4; 530/387.1; 436/13

(56) References Cited

FOREIGN PATENT DOCUMENTS

| 0 433 088 A1 | 6/1991 | (EP) . |
|---|---|---|
| WO 98/12561 | 4/1998 | (WO) . |
| PCT/GB98/00677 | 10/1998 | (WO) . |

OTHER PUBLICATIONS

Palinski et al., J. Clinic. Investigation, 98(3), 800–814, Aug. 1, 1996.*
Palinski et al. Low density lipoprotein undergoes oxidative modification in vivo, Proc. Natl. Acad. Sci. USA, vol. 86, pp. 1372–1376, Feb. 1989.
Palinski, et al. Antisera and Monoclonal Antibodies Specific for Epitopes Generated during Oxidative Modification of Low Density Lipoprotein, Arteriosclerosis; vol. 10, (1990) May/Jun. No. 3, pp. 325–335.

* cited by examiner

Primary Examiner—Anthony C. Caputa
Assistant Examiner—Bruce Tedeschi
(74) Attorney, Agent, or Firm—Foley & Lardner

(57) ABSTRACT

The invention relates to monoclonal antibodies which differentially bind oxidation-specific epitopes on lipoprotein in blood, arterial tissue and vascular tissue, including atherosclerotic plaque formed in arterial tissue and vascular tissue through lipoprotein oxidation. Methods for use of the antibodies in detecting and monitoring lipoprotein oxidation in vivo and in vitro are described, as are methods for inhibiting lipoprotein oxidation in vivo.

18 Claims, 7 Drawing Sheets

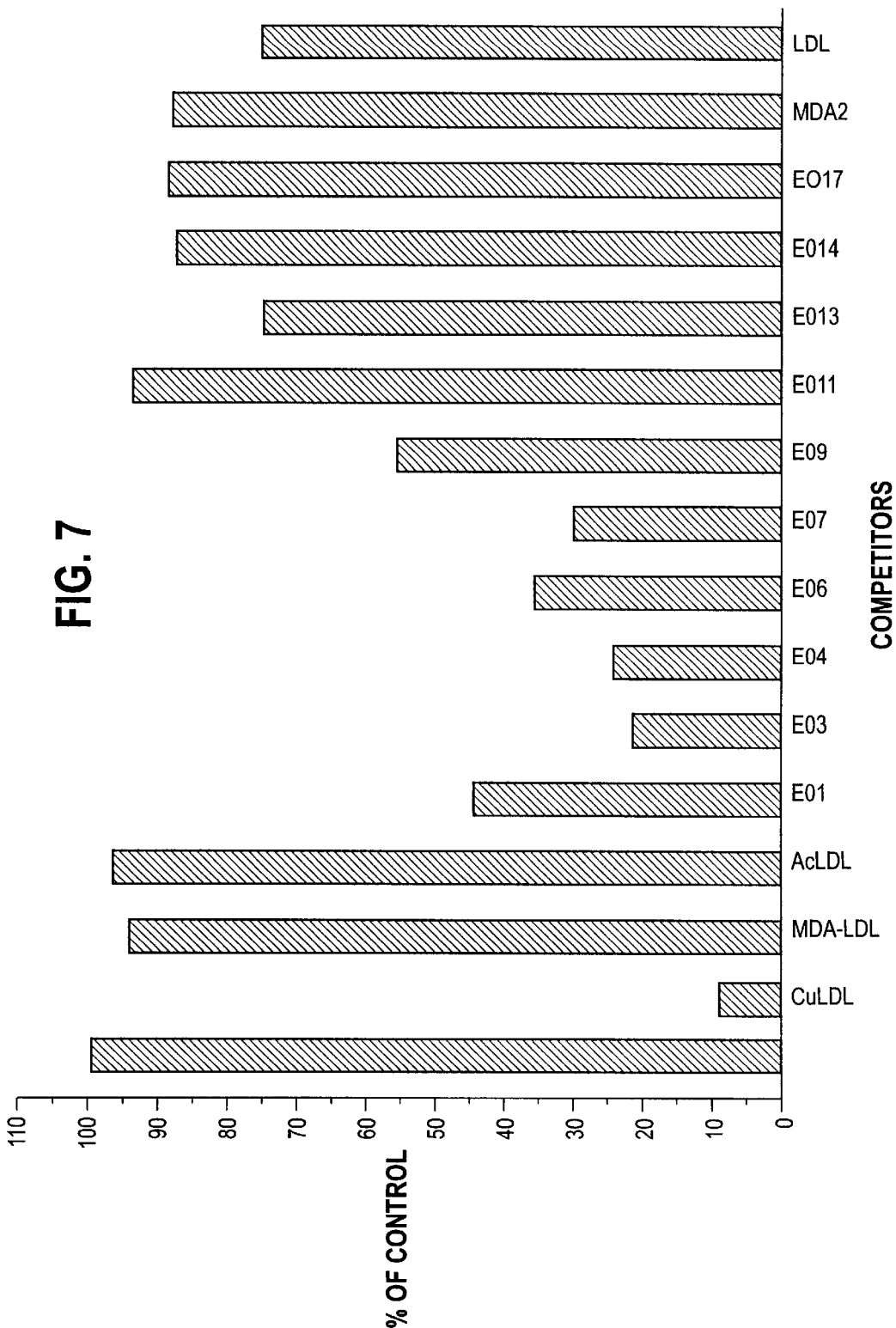

ANTIBODIES TO OXIDATION-SPECIFIC EPITOPES ON LIPOPROTEIN AND METHODS FOR THEIR USE IN DETECTING, MONITORING AND INHIBITING THE GROWTH OF ATHEROMA

STATEMENT AS TO FEDERALLY SPONSORED RESEARCH

This invention was made with government support under Grant Nos. HL57505-01 and HL14197-23 awarded by The National Institutes of Health. The government has certain rights in the invention.

FIELD OF THE INVENTION

The invention relates to monoclonal antibodies with binding specificity for oxidation-specific epitopes on lipoproteins in blood, coronary tissue and vascular tissue, including atherosclerotic plaque on such tissue. The invention further relates to methods for use of the monoclonal antibodies in detecting, monitoring and inhibiting the growth of coronary and vascular atheroma.

HISTORY OF THE INVENTION

Oxidation of blood lipoproteins and their deposition from blood into plaque is one of the major contributing factors in the onset of atherogenesis. For example, immunogenic oxidized low density lipoprotein (OxLDL) accumulates in plaque lesions of patients with atherosclerosis to form atheromas. Based on detection of autoantibodies to OxLDL, it also appears to be present in higher serum quantities than normal in patients with coronary artery disease, hypercholesterolemia, diabetes, peripheral vascular disease, hypertension and preeclampsia.

Candidate diagnostic reagents which have been investigated for binding to atherosclerotic plaque components include radiolabeled lipoprotein (LDL), polipoprotein B (apo B), autologous platelets, antifibrin antibodies and components related to smooth muscle cell proliferation. In general, however, such agents suffer from a lack of specificity and are not useful for monitoring the development of oxidation-specific epitopes on lipoproteins which arise during various stages of lipoprotein oxidation and atherosclerotic plaque formation.

SUMMARY OF THE INVENTION

The invention provides a panel of monoclonal antibodies ("E0 antibodies") that have unique binding specificity for one or more oxidation-specific epitopes on oxidized blood lipoproteins. The binding specificities of different antibodies for oxidation-specific epitopes which arise at various early and late stages of lipoprotein oxidation atheroma formation allows for early detection of plaque as well as monitoring of the oxidation process. To these ends, assay methods are provided by the invention that are based on in vivo and in vitro binding of oxidation-specific epitopes on lipoproteins by E0 antibodies in plasma and in plaque-lesioned tissue.

The E0 antibodies also bind particular oxidation-specific epitopes in a manner which inhibits macrophage-mediated incorporation of oxidized lipoproteins into developing plaque. Therapeutic methods which rely on the E0 antibodies to inhibit the formation of coronary and vascular atheroma are therefore also provided.

For in vitro diagnostic screening use, all or part of the panel of E0 antibodies are used to measure oxidation-specific epitopes in samples of host plasma or tissue. Expression and proliferation of oxidation-specific epitopes on lipoproteins of blood origin (especially LDL) correlates strongly with the onset and development of plaque lesions in coronary or vascular tissue. In addition, the appearance of epitopes which arise primarily during earlier or later stages of lipoprotein oxidation (which may be discriminated with certain members of the E0 antibody panel) is indicative of the stage of plaque lesion development in the host.

A host who screens positive for the presence of plaque lesions according to the invention is a candidate for further diagnostic evaluation to confirm the location of the lesions and the nature of the disease associated with the lesions (e.g., coronary artery disease). Furthermore, a host who screens positive for a diagnostically significant number of oxidation-specific epitopes induced by exposing a substantially nonoxidized lipoprotein sample from the host to a pro-oxidant is susceptible to plaque formation and a candidate for prophylactic treatment.

For in vivo diagnostic use, all or part of the panel of E0 antibodies are labelled with molecules that are detectable using in vivo imaging techniques and used as agents to image plaque lesions in coronary or vascular vessels.

For monitoring responsiveness to therapy or progression of lipoprotein oxidation, in vitro or in vivo measurements of oxidation-specific epitopes on lipoproteins in plasma or plaque are taken periodically using the same E0 antibodies for each measurement. In general, a decline in oxidation-specific epitope proliferation correlates to a decline in oxidative modification of lipoproteins. The decrease in the availability of oxidized lipoproteins for incorporation into plaque is indicative of a slowing or regression of the oxidation process which leads to atheroma formation. Conversely, increases in these values indicates that atheroma formation is proceeding in the evaluated host.

For use in the in vitro methods of the invention, the invention provides a sensitive sandwich immunoassay. The assay utilizes oxidation-protected LDL or HDL in a plasma or tissue sample obtained from a host in a sandwich with an antibody specific for a component of the lipoproteins and an E0 antibody. Existing oxidation-specific epitopes are measured using this assay technique. Alternatively, a susceptibility to lipoprotein oxidation in a host can be determined by detecting and measuring the type and number of oxidation-specific epitopes which are induced in response to adding a pro-oxidant to the host lipoprotein sample.

(specific for MDA-lysine) and NA59 (specific for 4-HNE-lysine) is shown in C. For comparison, FIGS. 2(D–F) depict the results of a competitive radioimmunoassay performed with various E0 antibodies and proteins as competitors of E0 antibodies and acrolein modified proteins to compete with E014 for binding to MDA-modified LDL. The acrolein modified proteins are: Acro LDL NR (nonreduced) and Acro LDL R (reduced), consisting of LDL extensively modified with 80 mM acrolein under nonreducing and reducing conditions, respectively; Acro BSA NR and Acro BSA R, consisting of BSA modified with acrolein under nonreducing and reducing conditions, respectively. Results are expressed as $B/B_0$, as described with respect to FIG. 1.

Figure 3:
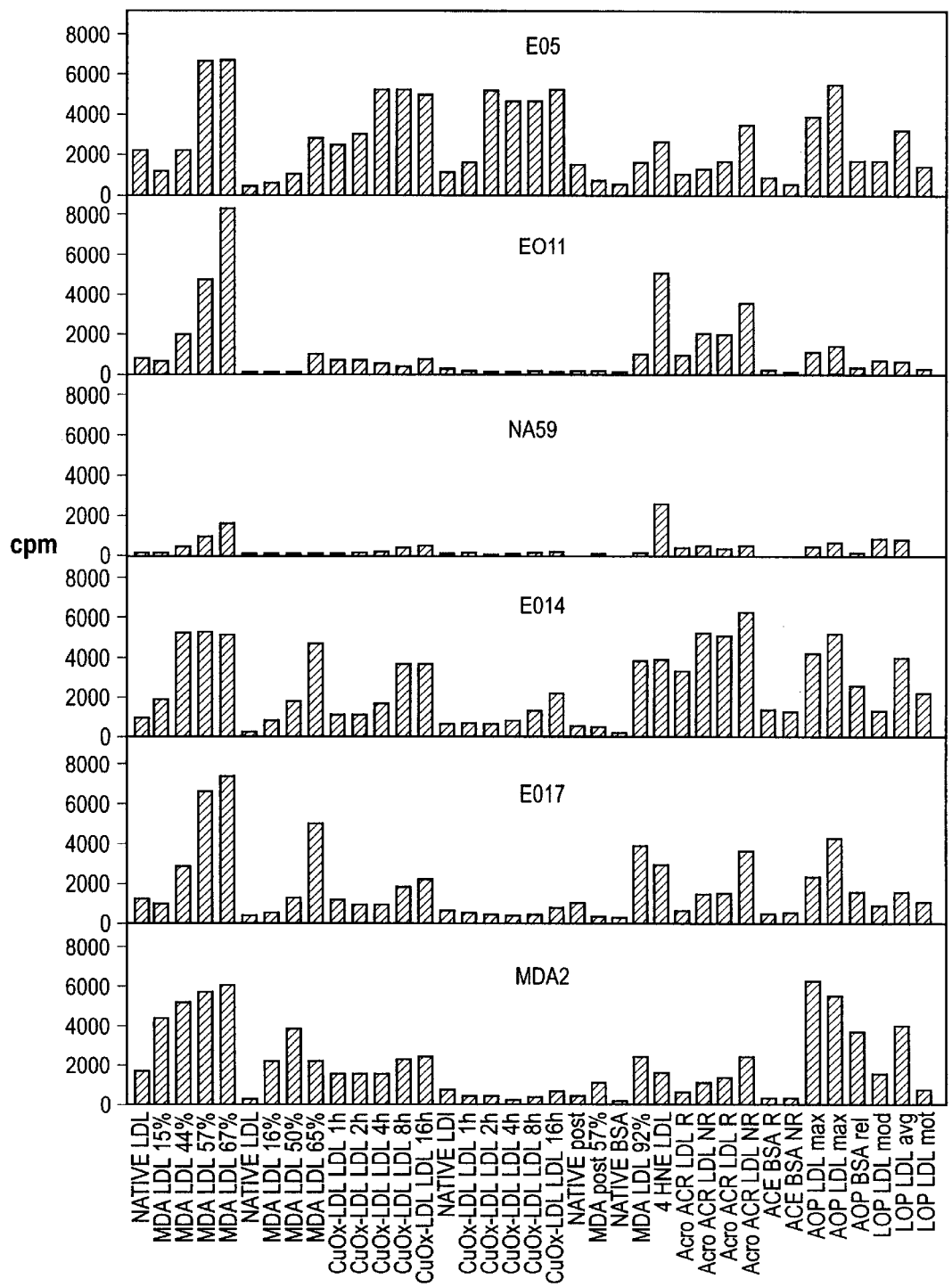

FIG. 3 is a graph depicting the results of a capture assay to measure binding by various E0 antibodies to different native and modified antigens. Abbreviations used in the Figure are MDA-HDL, high density lipoprotein modified with MDA; MDA-BSA, BSA modified with MDA; CuOx-LDL (or -HDL), LDL (or HDL) oxidized with 5 $\mu$M copper (for these preparations, the numbers refer to the extent of lysine modification or to the time of oxidation); Acro LDL (or BSA) NR and Acro LDL (or BSA) R, LDL (or BSA) modified with acrolein under nonreducing or reducing conditions (the concentration refers to the amount of acrolein used); AOP-LDL (or BSA), LDL (or BSA) extensively modified by arachidonic acid oxidation products; LOP-LDL (or BSA), LDL (or BSA) extensively modified by linoleic acid oxidation products.

Figure 4:
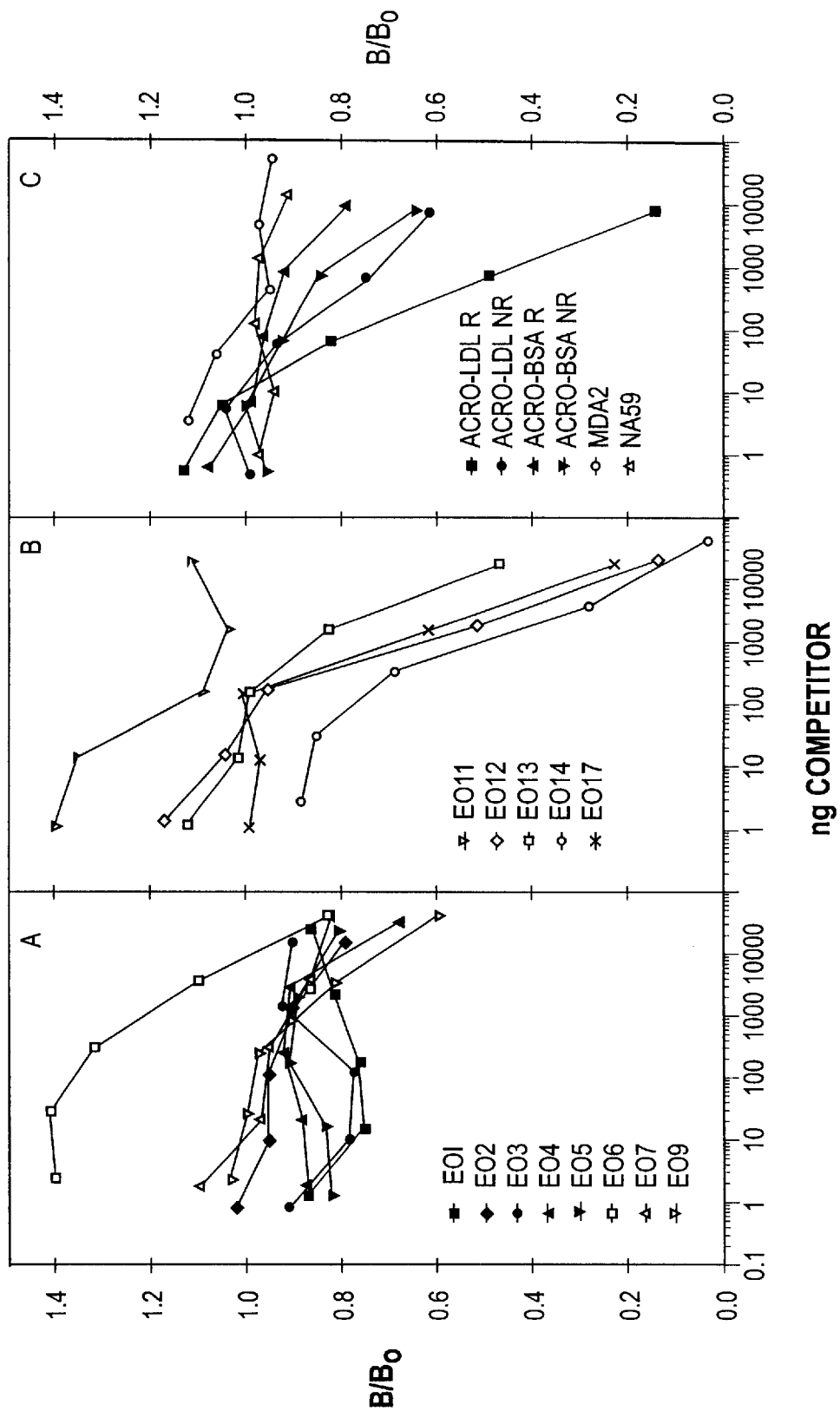

FIGS. 4(A–C) is a graph depicting the results of a competitive radioimmunoassay performed with various E0 antibodies and proteins as competitors of E014 for binding to acrolein-LDL. Competition by E0 antibodies originally selected for binding to copper-oxidized LDL is shown in A, and by E0 antibodies selected for binding to MDA-LDL or native LDL in B. Competition by acrolein-modified proteins and monoclonal antibodies MDA2 (specific for MDA-lysine) and NA59 (specific for 4-HNE-lysine) is shown in C.

Figure 5:
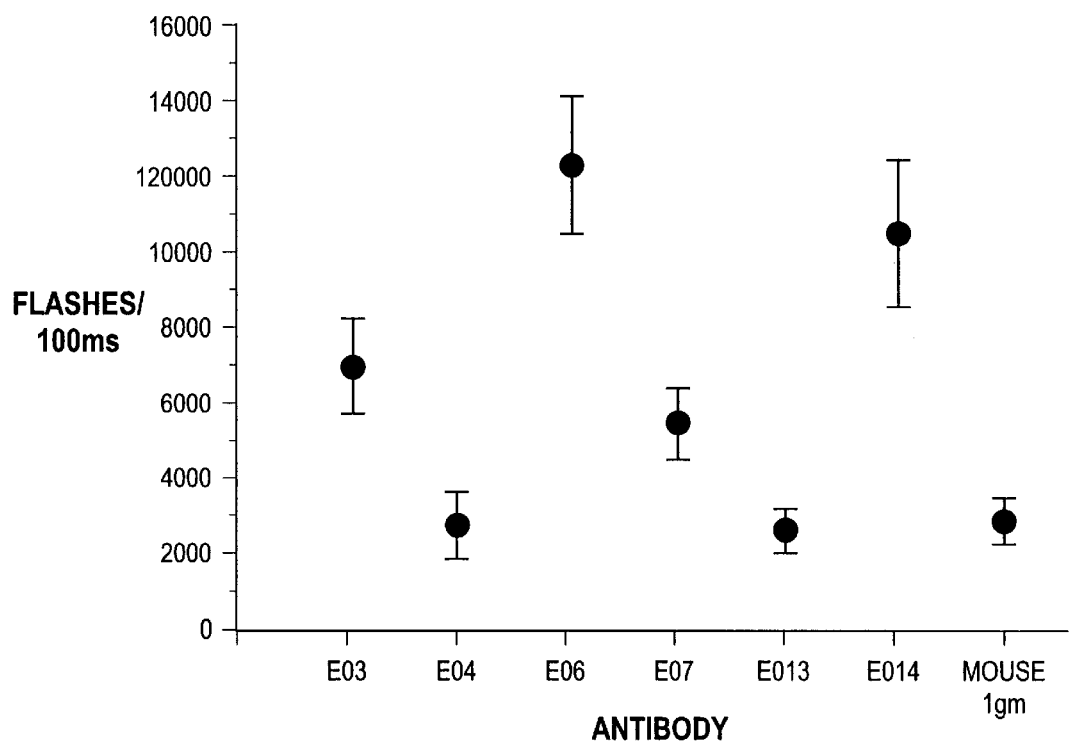

FIG. 5 is a graph depicting the results of a capture assay to measure binding of epitopes of OxLDL on circulating LDL by E0 antibodies. As a control, non specific mouse IgM was used in place of the E0 antibodies. Data shown are mean±standard deviation of plasma of seven different subjects. Results are reported as flashes of light/100 ms.

Figure 6:
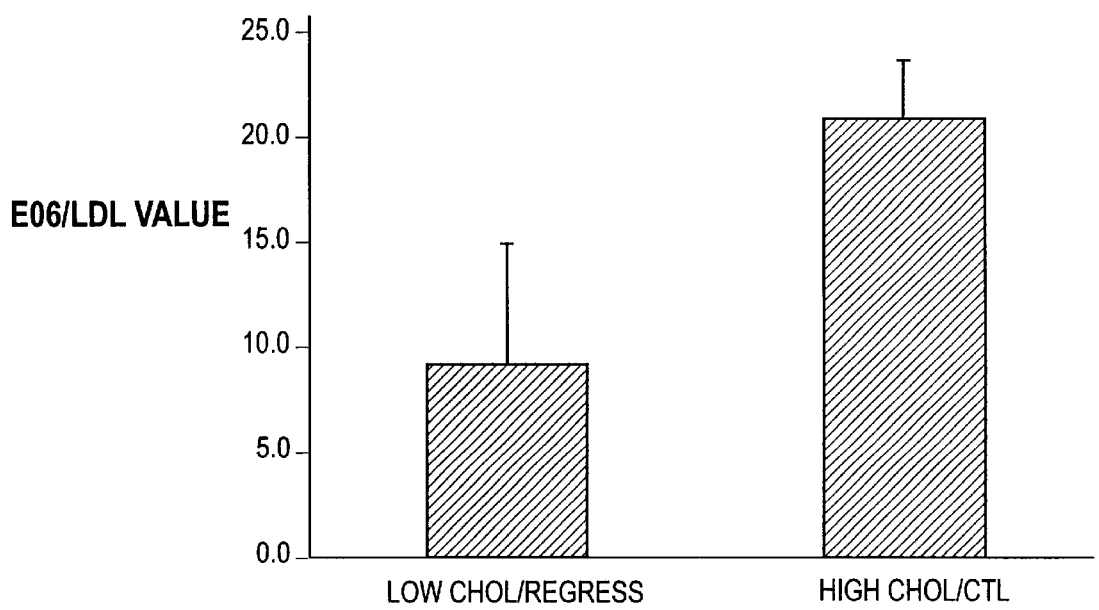

FIG. 6 is a graph depicting the results of a capture assay to measure binding of OxLDL in primate serum by E0 antibodies. Abbreviations used are: Low Chol/Regress, for serum titers in primates treated for high cholesterol levels with a low cholesterol diet; and High Chol/Ctl, for control, untreated animals.

FIG. 7 is a graph depicting the results of a competitive radioimmunoassay performed with various E0 antibodies and proteins as competitors for binding of OxLDL by macrophages.

DETAILED DESCRIPTION OF THE INVENTION

I. Antibodies With Binding Specificity for Oxidation Specific Epitopes on Oxidized Lipoprotein The present invention provides monoclonal antibodies (E0 antibodies) for in vivo and in vitro use which specifically target oxidation-specific epitopes, such as those occurring in oxidatively modified LDL and HDL, in blood and in atherosclerotic plaque lesions. As used in the disclosure, "antibodies" includes the E0 antibodies described, antibodies having the same binding specificity as those described, antibody fragments having the same binding specificity as those described, humanized antibodies having the same binding specificity as those described and chimeric antibodies having the same binding specificity as those described. Methods for producing such antibodies are detailed in Section IV of this disclosure and are exemplified in the Examples.

By the term "binding specificity" is meant the ability of an antibody to recognize and bind a specific antigenic epitope. A highly specific antibody binds its antigenic epitope with high affinity, e.g., the target epitope is bound with virtual exclusivity. For convenience, this discussion will focus on antibodies with binding specificity for LDL, which predominates over HDL in atherogenesis. However, the invention will be understood not to be limited to antibodies having LDL binding specificity.

When LDL undergoes lipid peroxidation, the peroxidized product reacts with lipids, apoproteins and proteins, generating immunogenic neoepitopes and epitopes. Resulting OxLDL-bound antigens formed at different stages of atherogenesis include malondialdehyde (MDA)-LDL (bound to lysine residues on apolipoprotein B (apoB) forming OxLDL), 4-hydroxynonenal (4-HNE)-LDL (bound to lysine residues on ApoB forming OxLDL), acetyl-LDL, acrolein-LDL (Acro LDL) and LDL modified with arachidonic or linoleic acid containing phospholipid oxidation products (respectively, AOP-LDL and LOP-LDL). Specific epitopes may be formed during different stages of lesion development and/or at certain sites within lesions, or conservation of epitopes may occur differentially at different sites.

OxLDL becomes incorporated into plaque lesions during atherogenesis when excess plasma LDL enters the arterial wall at lesion-prone areas and becomes oxidatively modified by various cell types (e.g., endothelial cells, macrophages and fibroblasts). Resident macrophages take up OxLDL, resulting in the foam cell formation which characterizes the lesions formed in the early stages of atherogenesis. Over time, the foam cells are degraded, releasing lipids into the extracellular space where an atheroma forms. Atherosclerotic plaque grows, in part, by incorporating and oxidizing additional lipoprotein.

Proliferation of oxidation-specific epitopes is believed to correlate to the degree of atherogenesis occurring in a host (based on detection of high titers of autoantibodies against oxidation-specific epitopes in the plasma of humans, rabbits, and mice). Higher titers of such autoantibodies are found in patients with increased carotid atherosclerosis, coronary artery disease, diabetes, peripheral vascular disease, hypertension, and preeclampsia.

Surprisingly, monoclonal antibodies with autoantibody-like binding specificity for a number of different oxidation-specific epitopes on lipoprotein (EO antibodies) can be produced in high titers from mice deficient in apolipoprotein E ("apo E"). Such mice spontaneously develop marked hypercholesterolemia and severe atherosclerosis. E0 antibodies have binding specificities for different epitopes on oxidized lipoprotein which arise at various stages of its oxidation and incorporation into atheroma.

Table I summarizes the binding characteristics displayed in vitro by E0 antibodies with respect to various OxLDL antigens, including copper ($Cu^{2+}$) oxidized LDL antigen, MDA-LDL antigen and various protein-LDL and oxidized phospholipid antigens.

TABLE I

IN VITRO BINDING BY E0 ANTIBODIES OF OxLDL ANTIGENS

| ANTIBODY | ANTIGEN | APPARENT BINDING SPECIFICITY |
|---|---|---|
| E01, E02, E03, E04 E05, E06, E07 and E09 (Group 1) | $Cu^{2+}$ oxidized LDL | $Cu^{2+}$ oxidized LDL epitopes formed progressively during the first 4 hours of oxidation; essentially same affinity for all recognized epitopes. None but E06 effectively bind MDA-LDL or 4-HNE-LDL (FIG. 1 and FIG. 4 [for E06]) |
| E012, E013, E014, E017 (Group 2) | MDA-LDL | MDA-LDL and, to a lesser extent, 4-HNE- LDL and Acro LDL; E013 also binds $Cu^{2+}$ oxidized LDL (FIGS. 1, 4 and 5) |
| E04 | $Cu^{2+}$ oxidized LDL | High and low density $Cu^{2+}$ oxidized lipoprotein (HDL, LDL). Competes with group-mates (except E05) fairly equally (FIGS. 2 and 3) |
| E014 | MDA-LDL | MDA-LDL ($\geq 70\%$ modified); 4-HNE-LDL Competes for binding with all group-mates and with MDA-lysine; 4-HNE-lysine (FIGS. 4 and 5) |
| E06 | $Cu^{2+}$ oxidized LDL | $Cu^{2+}$ oxidized LDL and HDL at 2–16 hours of oxidation; MDA-LDL ($\geq 70\%$ modified); APO-LDL; 80mM AcroLDL (nonreduced only); LDL (but not HDL) (FIGS. 1, 3, 4 and 5) |
| E011 | LDL | MDA-LDL ($\geq 40\%$ modified); 4-HNE-LDL; 80mM modified Acro LDL (reduced and nonreduced) (FIGS. 1, 3, 4 and 5) |
| E017 | MDA-LDL | MDA-LDL (all levels of modification); MDA- HDL ($\geq 50\%$ modified); $Cu^{2+}$ oxidized LDL (at 8 and 16 hours of oxidation); Acro LDL (20mM and 80mM reduced and nonreduced); AOP-LDL and LOP-LDL (at mid- to maximal levels of oxidation); 4-HNE-LDL (FIGS. 1, 3, 4 and 5) |

E06, E011 and E017 also bound MDA modified to 90% of the control antigen (bovine serum albumin [BSA]). No antibody bound BSA alone.

In vivo, OxLDL is concentrated primarily in atherotic lesions, with some minimally modified forms in circulation. Binding of the E0 antibodies to lesions and to circulating LDL is as follows:

TABLE II

IN VIVO BINDING BY E0 ANTIBODIES OF OxLDL IN LESIONS AND IN CIRCULATION

| STAGE OF LESION | ANTIBODIES | APPARENT BINDING SPECIFICITY |
|---|---|---|
| None (normal vessel) | All | No binding to tissue |
| Early | All | Primarily foam cells |
| Transitional | All | Foam cells; stronger binding in outer layers (e.g., macrophage-associated shoulder and cap regions) of the lesion; diffuse binding in necrotic core (E06 binds the outer layers and core region somewhat more extensively than its group-mates) |
| Advanced | E01, E03, E04, E06 E07 and E09 | Similar binding pattern among all antibodies, with most extensive binding in the core region, lesser binding in the outer layers. E06 bound the core region slightiy more strongly than its group-mates |

TABLE II-continued

IN VIVO BINDING BY E0 ANTIBODIES OF OxLDL IN LESIONS AND IN CIRCULATION

| STAGE OF LESION | ANTIBODIES | APPARENT BINDING SPECIFICITY |
|---|---|---|
| Advanced | E011 | Core region only |
| Advanced | E014 | Outer layers only |
| Advanced | E017 | Weak binding to outer layers and core region |
| Circulating LDL | E06 and E014 | Bound circ-LDL 3 to 4 times more extensively than other E0 antibodies |
| Circulating LDL | E03 and E07 | Bound circ-LDL |
| Circulating LDL | E04 and E13 | No greater binding than exhibited by non-specific IgM control |

As demonstrated by the data in the foregoing Tables (also described in FIG. 8 and Example V), several of the E0 antibodies of the invention demonstrate different binding specificities for epitopes which emerge at different stages of atherogenesis. Group 1 antibodies (E01 to E09) displayed similar affinities for all $Cu^{2+}$ oxidized LDL epitopes and, by extrapolation from E04 binding data, $Cu^{2+}$ oxidized HDL epitopes. These affinities arise early in the oxidation process, making the antibodies useful in the detection of early-stage lesions. Also, because the binding specificity of the antibodies in this group of antibodies is maintained throughout the oxidation process, the antibodies are useful for monitoring lesion progression.

For example, E06 has binding specificity for particular lysine and phospholipid epitopes on OxLDL (but not OxHDL) at relatively advanced stages of their development. Specifically, E06 binds MDA-LDL when at least 70% of the lysine residues on LDL are bound by MDA; binds nonreduced AcroLDL at relatively high levels of saturation; and, more weakly, binds APO-LDL.

In vivo, all of the Group 1 antibodies display similar affinities for similar regions of atherotic lesions. In the early stage of lesion development, the antibodies bind foam cells. Binding also appears in the necrotic core of the lesion as its development advances. Core binding by E06 is slightly higher than core binding by its group mates at both the transitional and advanced stages of lesion development.

Binding specificities among the antibodies of group 2 (E011 to E017) are more variable. All bind MDA-LDL, although only E017 binds the epitope at less than 40% MDA saturation. All also bind 4-HNE-LDL, demonstrating binding specificities similar to the previously described MDA2 antibody that binds the MDA-lysine adduct of LDL, as well as to the NA59 antibody, which binds the 4-HNE-lysine adduct of LDL. E011 also binds AcroLDL at relatively high levels of saturation in both the reduced and nonreduced states.

E017 also has binding specificity for particular lysine and phospholipid epitopes on OxLDL (and on OxHDL) at even relatively early stages of their development. Specifically, E017 also bound MDA-HDL when at least 50% of the HDL lysine residues were bound by MDA; AcroLDL at even relatively low levels of saturation in both the reduced and nonreduced states; AOP at at least about 50% oxidation and LOP at at least about 50% oxidation. E017 also bound $Cu^{2+}$ oxidation epitopes at relatively late stages of development.

In vivo, the pattern of early and transitional stage lesion binding by the group 2 antibodies was similar to the binding pattern displayed by the group 1 antibodies. In advanced lesions, however, the group 2 antibodies are more discriminate, with E011 binding only the core region, E014 binding only the outer region and E017 only weakly binding either region. The group 2 antibodies are therefore particularly useful for detecting advanced stage lesions and in discriminating among different layers within such lesions.

The affinity of the E06 and E014 antibodies for LDL undergoing very early stage oxidation in plasma makes these antibodies useful in determining the susceptibility of an individual to LDL oxidation and probable atherogenesis even before lesions begin to form. Individuals whose lifestyle, physical condition or family history place them at an increased risk of atheromas will benefit from the early treatment which may be followed on detection of minimally oxidized LDL in circulation with antibodies having the binding specificities of E06 and E014.

II. Exemplary Methods for Use of the E0 Antibodies

A. Method for In Vivo Diagnosis of, and Determination of Susceptibility to, Atheroma Formation in Coronary and Vascular Tissue To use E0 antibodies for the in vivo detection of atheroma-forming plaque, an E0 antibody is detectably labeled as described below in Section II.B of this disclosure. The E0 antibody is given to a host in a dose which is diagnostically effective. The term "diagnostically effective" means that the amount of E0 antibody is administered in sufficient quantity to enable detection of cardiovascular sites having plaque lesions.

Imaging post-injection is preferably made immediately following to about 24 hours after injection of the antibody, depending on the half-life of the radiolabel used and condition of the patient. Increased binding of detectably labeled antibody relative to a control (e.g., data evidencing the binding characteristics of the antibody to normal tissue) is indicative of the presence of atherosclerotic plaque in host cardiovascular tissue.

As a rule, the dosage of detectably labeled E0 antibody for in vivo diagnosis will vary depending on such factors as age, sex, and extent of disease of the individual. The dosage of E0 antibody can vary from about 0.01 $mg/m^2$ to about 500 $mg^2/m$, preferably 0.1 $mg/m^2$ to about 200 $mg/m^2$, most preferably about 0.1 $mg/^2$ to about 10 $mg/m^2$. Such dosages may vary, for example, depending on whether multiple injections are given, tissue, and other factors known to those of skill in the art.

The dosage of radioisotope label required to detect OxLDL in atherosclerotic plaque in a host will also vary with the radioactivity of the radioisotope and will be taken into account in determining a suitable dose to be given of an imaging antibody according to the invention. For example, the mean lethal dosages of both $^{125}I$ and $^{123}I$ have been calculated at about 79+/−9 cGy (in Chinese hamster ovary cells; see, e.g., Makrigiorgos, et al., *Radiat.Res.*, 118:532–544). For diagnostic purposes, the dosage will be less than the mean lethal dose for the radioisotope.

For example, with respect to the half-life of common radioisotopes, the half-life of $^{123}$I at a dose between 1 and 20 microCi (mCi) is about 13 hours, while the half-life of $^{123}$I at a dose of less than 5 mCi is about 8 days. With respect to positron emitters, the half-life of $^{11}$C at a dose of 200 mCi or more is only 20 minutes, while the half-life of $^{18}$F at a dose of only 50 mCi is nearly six times as long. For example, it is expected that a useful dose of $^{123}$I-labeled antibody would be between 1 and 20 mCi, while less than 5 mCi of the longer-lived $^{131}$I would be used (e.g. 0.5–5 mCi) and approximately 200 mCi $^{11}$C can be used (e.g., 100–300 mCi). Thus, for use according to the invention, the preferred dose of agents including radioisotopes with longer half-lives will be less than the preferred dose of agents including radioisotopes with shorter half-lives.

One of ordinary skill in nuclear medicine would know to take the above and other salient characteristics of the radioisotopes into account when calculating an appropriate dosage. As a general matter, it is expected that a useful dose of detectably labeled antibody would deliver between about 0.5 and about 500 millicuries (mCi). In general, this dosage range will not vary substantially with the weight, age and sex of the host. However, in juvenile hosts, dosages in the lower spectrum of each preferred dosage range will be preferred, in order to limit accumulation of radioactivity in dividing cells.

Selection and modification of particular doses for each detectably labeled E0 antibody to be used in the invention is within the ordinary level of skill in the art. In particular, dosimetry calculations are well-known in the art which permit estimation of the distribution and radioactive burden to host tissues and cells on administration of radioisotopes. For review in this regard, those of skill in the art may wish to consult Makrigiorgos, et al., *J.Nucl.Med.*, 31:1358–1363, 1990, the disclosure of which is incorporated herein by this reference to illustrate knowledge in the art concerning dosimetric calculations of radioactivity distribution. Suitable animal models of atherosclerosis for use in evaluating the characteristics and efficacy of particular pharmaceutical agents are described in Example II.

The detectably labeled E0 antibodies of the invention will be administered by a parenteral route selected to best target the suspected site of plaque formation; i.e., intravascular or intra-arterial injection. Antigen administered to enhance clearance of residual radioactivity in background (blood) will be administered by the same routes utilized to administer the antibody.

For monitoring the course of atherogenesis in a host as well as the host's responsiveness to therapy, the site of plaque formation may be imaged according to the invention more than once. Clearance of any previously administered radioactive agents (including those of the invention and chemotherapeutic agents) should be considered to limit detection of residual radioactivity. Rates of clearance may be determined based on known clearance rates for the particular radioisotopes present, or may be inferred by reimaging the host prior to readministering a detectably labeled E0 antibody according to the invention. Accumulation of the detectably labeled E0 antibodies of the invention in background will also be taken into account in this regard to maximize the target-to-background radioactivity ratios achieved in each imaging session.

Protocols and formulas for use in determining target-to-background ratios for radioactivity are well-known in the art. Depending on the radioisotope present, the detectably labeled E0 antibody may accumulate to some degree in tissues adjacent or distant from target tissues. Preferably, where possible, detectably labeled E0 antibodies will be chosen which do not accumulate at high levels in background tissues adjacent to suspected or known lesions of plaque formation (as compared to accumulation of the agent in more distant background tissues). Nonspecific binding of the detectably labeled antibodies of the invention is minimized by the high binding specificity of the antibodies for target OxLDL epitopes in atherosclerotic plaque.

A particularly advantageous method for reducing residual radioactivity in the background (i.e., blood) without interfering with antibody binding to target plaque using OxLDL antigens such as $Cu^{2+}$ oxidized LDL, MDA-LDL or 4-HNE-LDL. According to this aspect of the invention, the epitope antigen of the E0 antibody imaging agent is coupled to a protein carrier (e.g., albumin or lysine) and injected into the bloodstream of the patient after injection of the imaging antibody. The time lapse between injection of the imaging antibody and injection of the antigen will vary depending on the time following injection when images are to be obtained, but will preferably be performed at least an hour following injection of the antigen to maximize removal of residual imaging antibody from plasma.

B. Labeling of E0 Antibodies for in Vivo Imaging of Atherosclerotic Plaque

In vivo diagnostic imaging according to the invention is performed using E0 antibodies as described above which have been detectably labeled; i.e., joined to a radioisotope whose presence in the body may be identified using a detection instrument. Those of ordinary skill in the art will be familiar with, or can readily ascertain the identity of, techniques and instruments for in vivo detection of radioactivity provided in the host by detachably labeled E0 antibodies used according to the invention.

To detect radioactivity provided by gamma emitter detectably labeled E0 antibodies, an instrument commonly known as a gamma camera (i.e., a system of scintillation crystals or photo multiplier tubes for analysis of radioactive decay) will be used to detect gamma emission from the detectably labeled E0 antibody. To detect radioactivity provided by positron emitter detectably labeled E0 antibodies, techniques and instruments for positron emission tomography (PET) and single photon positron emission spectography (SPECT) are available to, and well-known in, the art. Those of ordinary skill in the art will also recognize that the E0 antibodies of the invention may be coupled to paramagnetic isotopes for use in magnetic resonance imaging (MRI), may be coupled to paramagnetic isotopes for use in electron spin resonance (ESR) or may be covalently attached to contrast media for use in ultrasound. In general, any conventional method for visualizing diagnostic imaging can be utilized.

The selection of a detectably labeled E0 antibody and detection technique suitable for a given application is within the ordinary level of skill in the art. Factors to be considered in this respect include the existence of any host sensitivity to a particular radioisotope, in vivo toxicity and efficiency of such molecules, potential pharmaceutical interactions between the detectably labeled E0 antibody and other medications taken by the host, the availability of particular detection instruments, and cost of materials.

Thus, for in vivo diagnostic imaging, the type of detection instrument available is a major factor in selecting a given labeling agent. For radioactive labeling agents, the radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylene triaminepentacetic acid (DTPA) and ethylenediaminetetraacetic acid (EDTA) and similar molecules.

Typical examples of radioisotopes which can be bound to the E0 antibodies of the invention are $^{111}$In, $^{97}$Ru, $^{67}$Ga, $^{68}$Ga, $^{72}$As, $^{89}$Zr, $^{90}$Y, $^{201}$Tl, $^{157}$Gd, $^{55}$Mn, $^{162}$Dy, $^{52}$Cr, $^{56}$Fe, $^{122}$I, $^{123}$I, $^{124}$I, $^{125}$I, $^{126}$I, $^{131}$I, $^{80}$mBr, $^{82}$Br, $^{75}$Br, $^{76}$Br, $^{77}$Br, $^{80}$Br, $^{18}$Fl, $^{11}$C, $^{13}$N and $^{99m}$technetium. Particularly preferred for their safety and relative ease of use and detection are $^{111}$In and $^{99m}$technetium.

Those of ordinary skill in the art will be familiar with, or can readily ascertain, synthesis methods appropriate to the preparation of radioisotopically labeled E0 antibodies for use in the inventive method. For example, other suitable radioiodination labeling techniques are taught in Keough, et al, *J.Labeled Compound Radiopharm.*,14:83–90, 1978. In addition, techniques useful in labeling molecules with positron emitters (e.g., $^{18}$fluorine) are known in the art and include the technique disclosed in Ishiwata, et al., *Eur.J.Nucl.Med.*, 9:185–189, 1984 ($^{18}$fluorine labeling of deoxyuridine). Techniques for labeling with non-halogen radioisotopes (such as $^{11}$C) are also well-known and include the technique referred to in Kubota, et al., *Jpn.J. Cancer Res.*, 80:778–782, 1989.

For in vitro use, there are many different labels and methods of labeling known to those of ordinary skill in the art. Examples of the types of labels which can be used in the present invention include enzymes, radioisotopes, fluorescent compounds, colloidal metals, chemiluminescent compounds, and bio-luminescent compounds. Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies. Those of ordinary skill in the art will know of other suitable labels for binding to the E0 antibodies of the invention, or will be able to ascertain such, using routine experimentation. Furthermore, the binding of these labels to the E0 antibodies of the invention can be done using standard techniques common to those of ordinary skill in the art.

C. Methods for In Vitro Use of the E0 Antibodies to Bind Oxidation-Specific Epitopes on Lipoprotein The E0 antibodies are especially useful in vitro for purposes of diagnosis (by identifying plaque as an atherosclerotic lesion), prognosis (by using a panel of E0 antibodies having differential binding specificities for OxLDL antigens at different stages of oxidation and development) and antigen/epitope identification (by identifying the presence of different antigen-induced OxLDL epitopes in a lesion). Conveniently, the antibodies are evaluated for OxLDL binding by immunoassay performed on a biological sample of plasma, coronary tissue or vascular tissue obtained from a host.

An especially useful sandwich immunoassay for capture of LDL from plasma and in vitro testing is a sensitive, double-capture chemiluminescent assay. In this assay, a standard IgG antibody or antibody fragment (preferably GAM-IgG Fc, a goat-anti-mouse IgG Fc fragment) is plated in wells of microtiter plates. Each well is then also plated with an antibody of known LDL and OxLDL specificity, such as monoclonal antibody MB47 (specific for one epitope on apo B) or MB24 (specific for a different epitope on apo B) ("OxLDL antibody"). The GAM-IgG Fc binds MB47 so as to maximize the expression of its two binding sites. The IgG and OxLDL antibody form the "bottom layer" of the immunoassay sandwich. Alternatively, the OxLDL antibody (e.g., MB47) can be plated directly to the microtiter plate wells.

Host plasma (preferably diluted; e.g., in a 1:50 dilution) is added to each plated well and incubated in each well for at least about an hour. Alternatively, lipoproteins eluted from a tissue biopsy in the presence of a buffer containing antioxidants and/or plasma (which contains natural antioxidants) can be used to isolate OxLDL from the sample. Antibody-captured LDL forms the middle layer of the "sandwich".

Each well is then extensively washed, preferably with antioxidant-containing buffers. Antigen corresponding to the OxLDL antibody plated in each well (e.g., apo B 501) is then added to each well and incubated for at least about another hour to saturate binding sites on the OxLDL antibody. Detectably labeled E0 antibodies are then added to separate wells in appropriate dilutions to form the top layer of the sandwich. After extensive washing with an automatic plate washer, the amount of E0 antibody bound (IgM) is detected by a goat anti-mouse IgM antibody labeled with a visually detectable molecule. As a control, non specific mouse IgM is used in place of the E0 antibodies.

Alternatively, E0 antibodies are tagged (e.g., biotinylated) and added directly to the LDL containing wells. After an appropriate period of incubation, the wells are washed and the amount of bound E0 antibody is measured using a detectable binding partner for the E0 antibody tag (e.g., biotin), such as avidin-labeled alkaline phosphatase, and a detection assay appropriate to detection of the binding partner used, such as a chemiluminescent technique.

Confirmation that LDL epitopes are bound by the E0 antibodies can be provided by "inverting" the sandwich. In the inversion format, the E0 antibodies are plated onto wells to form the bottom layer of the sandwich. Plasma or isolated LDL is added, followed by labeled OxLDL antibody (e.g., MB47) and, if desired, GAM-IgG Fc.

In separate and parallel wells, a labeled OxLDL antibody specific for a different, non-competing epitope (e.g., MB24) than the OxLDL antibody used in the assay (e.g., MB47) can be used in the top layer of the sandwich. Assay results may then be compared to verify that equal amounts of LDL were bound by the MB47 from each of the plasmas added; e.g., that under the assay conditions used, the amount of plasma or isolated LDL added saturates the capacity of MB47 binding.

So validated, the double capture immunoassay permits identification of the concentration of epitopes bound by each E0 antibody (Table I, above) per particle of LDL. Increased expression of such epitopes—particularly those which only appear in later stages of LDL peroxidation and adduct modification—can indicate an enhanced state of oxidation indicative of a progression of atherogenesis in the host. Similarly, the appearance of early stage OxLDL epitopes in a sample is indicative of the onset of atherogenesis. In addition, detection of OxLDL epitopes in circulating LDL is indicative of a susceptibility to further oxidation of LDL and atherogenesis.

For example, as shown by the data set forth in Example V, increased expression of E06 epitopes in the plasma of humans suffering from extensive coronary artery disease (confirmed by coronary catherization) and in hypercholesterolemic non-human primates was detected, as compared to healthy (vascular disease free) controls.

Susceptibility to LDL oxidation may be further defined by inducing various stages of oxidation in isolated LDL obtained from a host and detecting the development of oxidation-specific epitopes which arise during the artificial oxidation (e.g., by exposing the isolated LDL to copper or another known pro-oxidant for discrete intervals of increasing lengths of time). The number of epitopes bound by a particular E0 antibody per LDL particle may be quantified as described above. Rapid development of oxidation-specific epitopes in the host sample will be indicative of a susceptibility of the host to LDL oxidation in response to particular antigens in vivo.

The E0 antibodies and double-capture assay method of the invention are also useful in defining epitopes which are responsible for different stages of atherogenesis and screening for agents to inhibit oxidation-specific LDL epitope binding by macrophages (which leads to foam cell formation). In particular, the binding specificities of the E0 antibodies for foam cells in the early and transitional stages of atherogenesis permits their use (and the use of other monoclonal antibodies determined to have the same binding specificity as the E0 antibodies according to the methods described below in this disclosure) as competitors for macrophage binding to OxLDL epitopes.

Those of ordinary skill in the art will also be familiar with, or can readily identify, additional immunoassay formats of use with the E0 antibodies of the invention and OxLDL antigens. Examples of such immunoassays are competitive and non-competitive immunoassays in either a direct or indirect format. These formats include the radioimmunoassay (RIA), the standard sandwich assay and the Western blot assay. Each such format may be run in either the forward, reverse, or simultaneous modes, including immunohistochemical assays on physiological samples. The concentration of antigen and antibody which are used will vary depending on the type of immunoassay and nature of the detectable label which is bound to either the antigen or E0 antibody. Those of ordinary skill in the art will be able to readily ascertain suitable parameters for performing each immunoassay format suitable for use in the invention.

E0 antibodies can be bound to many different carriers and used to detect the presence of antigen epitopes antibody specifically reactive with each antibody. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention.

There are many different detectable labels and methods of labeling known to those of ordinary skill in the art. Examples of the types of labels which can be used in the present invention in addition to the radioisotopes and magnetic particles described in Section B above include enzymes, colloidal metals, fluorescent compounds, chemiluminescent compounds and bioluminescent compounds. Those skilled in the art will know of other suitable carriers and detectable labels, or will be able to ascertain such, using routine experimentation.

III. Therapeutic Methods for Use of E0 Antibodies to Inhibit Foam Cell Formation As previously noted, macrophages contribute to the formation of atheromas by binding and degrading oxidized lipoprotein to form foam cells, the precursors to atheroma formation. Through competition for binding at oxidization-specific epitopes on oxidized lipoprotein, E0 antibodies (or molecules which mimic their binding specificity) inhibit the formation of foam cells.

The term "inhibit" denotes a lessening of the rate of foam cell formation in a host as measured, for example, by detecting a slowing or cessation in the formation of oxidation-specific epitopes in the host's blood, arterial tissue or vascular tissue or by detecting a slowing or cessation in the growth of an atheroma. The term "therapeutically effective" means that the amount of E0 antibody used is of sufficient quantity to inhibit foam cell formation.

The dosage ranges for the administration of the E0 antibody are those large enough to produce the desired effect as measured by the above-referenced parameters using the assay methods described elsewhere above. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary from about 0.001 mg/kg/dose to about 2 mg/kg/dose, preferably about 0.001 mg/kg/dose to about 0.2 mg/kg/dose, in one or more dose administrations daily, for one or several days.

The E0 antibodies can be administered parenterally by injection or by gradual perfusion over time. Delivery can be intravenous, intraperitoneal, intramuscular, subcutaneous, intracavity, or transdermal. Efficacy of the therapy is determined and monitored by clinical signs of improvement in the host as well as by use of the in vivo and in vitro assay techniques described in this disclosure.

IV. E0 Monoclonal Antibodies: Methods for Preparation

A specific technique for generating monoclonal antibodies with the binding specificities of the E0 antibodies described herein is detailed in Example II. In general, techniques for making monoclonal antibodies are known and may be readily employed by those of ordinary skill in the art to generate monoclonal antibodies having the characteristics taught herein.

Hybridomas prepared from spleen cells of an immunized animal which secrete a desired monoclonal antibody can be produced in various ways using techniques well understood by those having ordinary skill in the art and will not be repeated in detail here. Details of these techniques are described in such references as *Monoclonal Antibodies-Hybridomas: A New Dimension in Biological Analysis*, edited by Roger H. Kennett, et al., Plenum Press, 1980; and U.S. Pat. No. 4,172,124, incorporated herein by reference.

Methods are also known in the art which allow antibody exhibiting binding for a preselected ligand to be identified and isolated from antibody expression libraries. Use of a murine library obtained from the ApoE-deficient mouse would yield a greatly enriched population of desired antibody binding domains because such mice spontaneously produce very high titers of E0 antibodies to oxidation specific epitopes. This methodology can be applied to hybridoma cell lines expressing monoclonal antibodies with binding for a preselected ligand.

For example, a method for the identification and isolation of an antibody binding domain which exhibits binding with a peptide of the invention is the bacteriophage λ vector system. This vector system has been used to express a combinatorial library of Fab fragments from the mouse antibody repertoire in *Escherichia coli* (Huse, et al., *Science*, 246:1275–1281, 1989) and from the human antibody repertoire (Mullinax, et al., *Proc. Natl. Acad. Sci.*, 87:8095–8099, 1990). As described therein, antibody exhibiting binding for a preselected ligand were identified and isolated from these antibody expression libraries.

In addition, methods of producing chimeric antibody molecules with various combinations of "humanized" antibodies are known in the art and include combining murine variable regions with human constant regions (Cabily, et al. *Proc. Natl. Acad. Sci. USA*, 81:3273, 1984), or by grafting the murine-antibody complementary determining regions (CDRs) onto the human framework (Riechmaim, et al., *Nature* 332:323, 1988). This invention therefore further provides chimeric E0 antibodies. Chimeric antibodies are constructed by recombinant DNA technology, and are described in, for example, Shaw, et al., *J. Immun.*, 138:4534 (1987), Sun, L. K., et al., *Proc. Natl. Acad. Sci. USA*, 84:214–218 (1987).

Briefly, any E0 antibody can be used to generate CDR grafted and chimeric antibodies. The analogous CDR sequences are said to be "grafted" onto the substrate or recipient antibody. The "donor" antibody is the antibody providing the CDR sequence, and the antibody receiving the substituted sequences is the "substrate" antibody. One of skill in the art can readily produce these CDR grafted antibodies using the teachings provided herein in combination with methods well known in the art (see Borrebaeck, C. A., *Antibody Engineering: A Practical Guide*, W. H. Freeman and Company, New York, 1992, incorporated by reference).

Under certain circumstances, monoclonal antibodies of one isotype might be more preferable than those of another in terms of their diagnostic or therapeutic efficacy. Particular isotypes of a monoclonal antibody can be prepared secondarily, from a parental hybridoma secreting monoclonal antibody of different isotype, by using the sib selection technique to isolate class-switch variants (Steplewski, et al., *Proc. Natl. Acad. Sci. U.S.A.*, 82:8653, 1985; Spira, et al., *J. Immunol. Methods*, 74:307, 1984). Thus, the invention includes class-switch variants of E0 antibodies having binding specificity comparable to that of any of the E0 antibodies described herein.

It is possible to determine, without undue experimentation, if a monoclonal antibody has the same specificity as an E0 antibody described herein by ascertaining whether the former prevents the latter from binding to a target oxidation-specific epitope. If the monoclonal antibody being tested competes for binding with the E0 antibody (as shown by a decrease in binding by the monoclonal antibody of the invention), then the two monoclonal antibodies bind to the same, or a closely related, epitope.

Still another way to determine whether a monoclonal antibody has the specificity of an E0 antibody of the invention is to pre-incubate the monoclonal antibody being tested with the oxidation-specific epitope to which the E0 antibody is reactive, then add the E0 antibody to determine if its binding to the oxidation-specific epitope is inhibited. If binding by the E0 antibody is inhibited then, in all likelihood, the monoclonal antibody being tested has the same, or functionally equivalent, epitopic specificity as the E0 antibody.

E0 antibodies can also be used to produce anti-idiotypic antibodies which can in turn be used to screen monoclonal antibodies to identify whether the antibody has the same binding specificity as an E0 antibody. An anti-idiotypic antibody is one which recognizes unique determinants present on a target antibody. Such determinants are located in the hypervariable region of the antibody. It is this region (paratope) which binds to a given epitope and, thus, is responsible for the specificity of the anti-idiotypic antibody.

An anti-idiotypic antibody can be prepared by immunizing an animal with an E0 antibody The immunized animal will recognize and respond to the idiotypic determinants of the immunizing E0 antibody and produce an antibody to these idiotypic determinants. By using the anti-idiotypic antibodies of the immunized animal, it is now possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using antiidiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to an E0 antibody will have a binding domain in the hypervariable region which is the "image" of the epitope bound by the E0 antibody. Thus, anti-idiotypic monoclonal antibodies can be used for immunization, since the anti-idiotype monoclonal antibody binding domain effectively acts as an antigen.

For in vivo administration, E0 antibodies will preferably be formulated in a pharmaceutically acceptable carrier, most preferably a liquid (see, standard reference Remington's Pharmaceutical Sciences, which is incorporated herein by reference to illustrate knowledge in the art concerning suitable pharmaceutical carriers). Exemplary liquid carriers are saline, Ringer's solution, syrup, peanut oil, olive oil and like emulsions. The formulation can be in the form of an aqueous or nonaqueous liquid suspension and may include pharmaceutically acceptable preservatives.

For use in vivo or in vitro, E0 antibodies can also be bound to many different carriers. Examples of suitable carriers include, for in vivo use, proteins (e.g., BSA and lysine) and, for in vitro use, glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

Examples illustrating practice of the method of the invention are set forth below. These examples should not, however, be considered to limit the scope of the invention, which is defined by the appended claims. In the examples, the abbreviation "min." refers to minutes, "hrs" and "h" refer to hours, "d" refers to days, "wk." refers to weeks, "i.v." refers to intravenous, "mAb" refers to monoclonal antibody, and measurement units (such as "ml") are referred to by standard abbreviations.

EXAMPLE I

Preparation of E0 Monoclonal Antibodies

E0 antibodies were obtained by fusing B-lymphocytes isolated from the spleens of two female 9-mo-old homozygous apo E-deficient mice with a myeloma cell line. These particular apo E-deficient mice were supplied from a colony established in La Jolla, Calif. from breeders provided by Dr. Jan Breslow (Rockefeller University, New York), and were hybrids with a C57BL/6 background. These mice were never immunized with an exogenous immunogen. They were fed a high fat diet (88137 Teklad Premier Laboratory Diets, Madison, Wis.) containing 12.8% milk fat and 0.15% cholesterol (without sodium cholate) for 7 mo. Such dietary intervention induces extensive aortic atherosclerosis, and is accompanied by the formation of high titers of E0 antibodies to MDA-lysine. Body weights of the two mice at 9mo. were 30.3 and 37.3 g, total plasma cholesterol levels were 1,513 and 2,321 mg/dl, and triglyceride levels were 64 and 260 mg/dl, respectively.

To verify the presence of antibodies to epitopes of OxLDL, pooled serum from both mice was screened for antibodies to native LDL, MDA-LDL, 4-HNE-LDL, and a mixture of 4-and 16-h Cu2+-LDL, using immunoassays described below. Primary screening of supernatants from hybridoma cell lines was performed after 10d of growth. Hybridomas were selected on the basis of the supernatant's ability to bind native or modified human LDL in solid phase RIAs. Screening antigens included MDA-LDL, 4-HNE-LDL, and a mixture of 4-and 16-h Cu2+-LDL generated as described in Example II.

Antibody specificities of hybridoma supernatants were determined by solid phase binding and competition RIA (described below). Of the 768 pooled samples tested, 64% were positive; i.e., showed binding to at least one form of OxLDL that was three fold greater than binding to native LDL. In other words, the percentage of original clones secreting antibodies to OxLDL was between 32 and 64%. Hybridoma cell lines contributing to the positive wells were then assayed individually, and hybridomas showing the greatest antibody binding were selected for cloning by limiting dilution.

Hybridoma cells were injected intraperitoneally into Pristane-primed Balb/C mice to produce ascites fluid. Immunoglobulin (Ig) subclasses were identified with a commercial isotyping kit (Mallory Laboratories, Springfield, Va.). The Ig was isolated by Sepharose 6HR10/30 chromatography in the presence of 100 mM Tris, 50 mM NaCl, pH 7.8, on a FPLC system (Pharmacia LKB Biotechnology Inc., Piscataway, N.J.). Fractions containing the Ig were identified immunochemically, concentrated in an Amicon 3050 stirred cell with a YM100 membrane Amicon Corp., Danvers, Mass.), and stored at −20° C.

Sera from two animals obtained at the time of sacrifice were pooled and screened for E0 antibodies to Cu2+-LDL, MDA-LDL, 4-HNE-LDL, and native LDL in solid-phase immunoassays with heavy chain-specific second antibodies. As expected, the pooled sera contained high titers of E0 antibodies binding to MDA-LDL, predominantly IgG and IgM (titers 5,000). In addition, high titers of E0 antibodies to 4-HNE-LDL and Cu2+-LDL (5,000), but not to native LDL were found. All of the E0 antibodies were isotyped as IgM, and were shown to be unique by isoelectric focusing. No significant titers of IgA antibodies to OxLDL epitopes were detected.

EXAMPLE II

Preparation of Artifactual Oxidation Protected Oxidazed Lipoprotein Antigens

Human LDL and HDL were freshly isolated from plasma of healthy human donors by sequential ultracentrifugation in the presence of high concentrations of antioxidants. Native LDL was stored at 4° C. and used within 2wk. LDL and other proteins were modified with MDA and 4-HNE using known techniques. The degree of modification of the lysine residues of apo B was determined by trinitrobenzenesulfonic acid assay. The extent of modification was also verified by comparing the electrophoretic mobility of the modified lipoproteins to that of native LDL, using 1% agarose gels (Corning Medical and Scientific, Palo Alto, Calif.) in borate buffer, pH 8.6. For the initial screening of hybridomas, extensively modified MDA-LDL was used (~75% of the lysine residues modified), whereas MDA-LDL preparations with varying degrees of modification were generated for the subsequent characterization assays.

Cu2+-LDL was generated by incubating 100 g LDL/ml PBS, pH 7.35, with 5M $CuSO^4$ at 37° C. for 1 to 16 h dialyzed against PBS containing EDTA, and concentrated using Centriflo cone-type membrane (CF25 Amicon Corp.). For the early screening of antibodies, a mixture of 4-and 16-h Cu2+-oxidized LDL was plated as antigen, to ensure that both early and late oxidation epitopes would be represented.

Modification of LDL or BSA with acrolein and that of BSA with several 2-unsaturated aldehydes was performed using known techniques. The degree of LDL modification by acrolein was varied by changing aldehyde concentration, time, and temperature as follows: 20 mM acrolein at 20° C. for 1 h and 80 mM acrolein at 20° C. for 2 h. BSA was modified with 50 mM acrolein, 50 mM 2-pentenal, 10 mM 2-heptenal, or 3 mM nonenal, for 4 h. In each case, parallel reactions were carried out in the presence of 200 mM $NaCNBH^3$, to reduce Schiff bases (aldimine) to amines, which favors the formation of adducts with the carbonyl group rather than the 3-position carbon. These preparations were labeled "reduced" (R) or "nonreduced" (NR). Excess aldehyde was removed by overnight dialysis at 4° C. against Dulbecco's PBS containing 10M EDTA.

Reactive products of fatty acid oxidation were also generated by thermal autoxidation of arachidonic acid or linoleic acid. 10 mg arachidonic acid or linoleic acid was transferred to a glass vial open to air and kept at 37° C. (arachidonic acid) or 100° C. (linoleic acid) for 72 h. The yellow-brown reaction products were dissolved in methanol and suspended by vigorous vortexing in 1 ml Dulbecco's PBS with 10M EDTA, pH 7.4. Aliquots containing the residue from 1–3 mg oxidized fatty acid were added to 0.5–1 mg LDL or albumin, and brought to a total volume of 1 ml with PBS. The ratio of weight of fatty acid oxidation products to protein was 3:1 for LDL or albumin adducts moderately modified with arachidonic oxidation products (AOP), and 6:1 for adducts extensively modified with AOP. The ratio was 6:1 for adducts of LDL or albumin moderately modified with linoleic oxidation products (LOP), and 12:1 for adducts extensively modified with LOP. Irreversible derivatization of proteins occurred within minutes at 20° C. and was substantially completed within a few hours.

After overnight incubation at 20° C., mixtures were dialyzed against PBS containing EDTA. As the lipid peroxidation products in these preparations may interfere with the trintrobenzenesulfonic acid assay, the percentage of lysine residues modified was estimated from the electrophoretic mobility of LDL, using an empirical relationship based on quantitation of lysine residues by amino acid analysis. The extent of modification of AOP- and LOP-modified BSA was not determined for the actual preparations, but results of previous studies showed that it was consistently similar to that of LDL modified under identical conditions. Acetyl-LDL was generated using known methods.

EXAMPLE III

Determination of E0 Antibody Titers and Specificity

Initial screening of plasma, hybridoma supernatants, ascites, and purified antibodies was performed with conventional solid-phase RIA techniques. For binding assays, 96-well polyvinylchloride microtitration plates (Dynatech Laboratories, Inc., Chantilly, Va.) were coated with of antigen (5 g/ml) in PBS containing 0.27 mM EDTA and 20M butylated hydroxytoluene overnight at 4° C. Non-adherent antigen was aspirated and remaining binding sites were "blocked" by incubation with 2% BSA (RIA grade, Sigma Chemical Co., St. Louis, Mo.) in PBS for 45 min at room temperature. The wells were washed four times with PBS containing 0.27 mM EDTA, 0.02% $NaN^3$, 0.05% Tween 20, and 0.001% aprotinin (washing buffer), using a microtiter plate washer. Serial dilutions of antibody in washing buffer containing 3% BSA (dilution buffer) were prepared, added at 50 µl/well, and incubated overnight at 4° C.

The amount of immunoglobulin bound was quantitated with affinity-purified goat anti mouse IgG or IgM Sigma Chemical Co.) labeled at 3,000–12,000 cpm/ng with $^{125}I$ using lactoperoxidase (Enzymobeads Bio-Rad Laboratories, Richmond, Calif.). Plates were incubated for 4 h at 4° C. with the secondary antibody, diluted to 400,000 cpm/50 µl dilution buffer.

In initial studies, sera from the two apo E-deficient mice used to generate the monoclonal antibodies and from two age-matched C57BL/6 mice were screened for circulating E0 antibodies against selected antigens, using the above described binding assay. For these studies, a titer was defined as the reciprocal of the highest dilution that gave binding to the antigen three times higher than binding to BSA. For subsequent studies, the actual dilution curves were used to define the titers.

Native LDL (0 time) was exposed to copper ions (5 µM) for indicated periods of time and then used to coat microtiter wells. 5 µl of each purified antibody were added per well, and antibody binding detected with $^{125}I$-labeled goat anti-mouse IgM.

The results of the studies comparing binding of each E0 antibody to progressively Cu2+-oxidized LDL are tabulated in Table I, above. In general, antibodies initially selected for predominant recognition of Cu2+-LDL (E01 to E09) recognized epitopes that were progressively formed during the first 4 h of oxidation of LDL. For many of the antibodies, the binding reached a plateau with LDL oxidized between 8 and 16 h. Antibodies initially selected primarily for their binding to "native" LDL (E011) or MDA-LDL (E013 to E017) bound poorly to this preparation of Cu2+-LDL, with the exception of E012 and E013.

Although some MDA-lysine epitopes are formed during Cu2+-oxidation, the strong binding of E012 and E013 suggested that these antibodies may recognize an epitope immunologically related to but structurally different from MDA-lysine. Some MDA-lysine epitopes may not be at the surface of MDA-modified LDL; however, upon delipidation, such epitopes may become available for E0 antibody binding.

Figure 1:
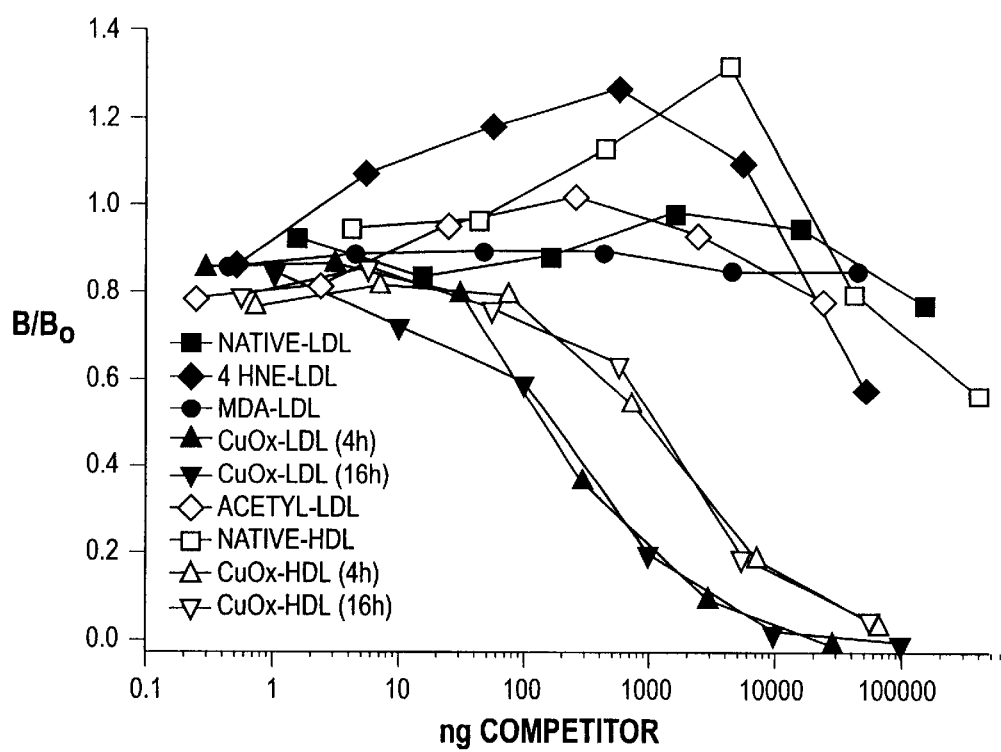
FIG. 1 is a graph depicting the results of a competitive radioimmunoassay performed with E04, originally selected for its binding to copper-oxidized LDL, using various forms of modified LDL and HDL. Results are expressed as binding of $^{125}$I-labeled E04 to the plated antigen in the presence of competitor (B) divided by binding in the absence of competitor ($B_0$). The competitors were copper oxidized (CuOx)-LDL and CuOx-HDL, copper-oxidized human LDL and HDL, respectively (the parentheses indicate the length of the time of incubation with copper); acetyl-LDL, human LDL modified with acetyl.

For further characterization of an antibody of the E01 through E09 group, E04 was purified from ascites, radiolabeled, and used at a limiting dilution in a competitive RIA with 16 h Cu2+-oxidized LDL as plated antigen. Referring to FIG. 1, complete competition was achieved by 4 and 16 h Cu2+-oxidized LDL, as well as by 4 and 16 h Cu2+-oxidized HDL, indicating that the epitope recognized by E04 is not specific for modified LDL alone. Rather, in certain respects, the specificity of E04 resembles that of OLF4-3C10, an induced monoclonal antibody previously generated by immunizing mice with apoprotein fragments of 4 and 18 h Cu2+-oxidized murine LDL.

Figure 2:
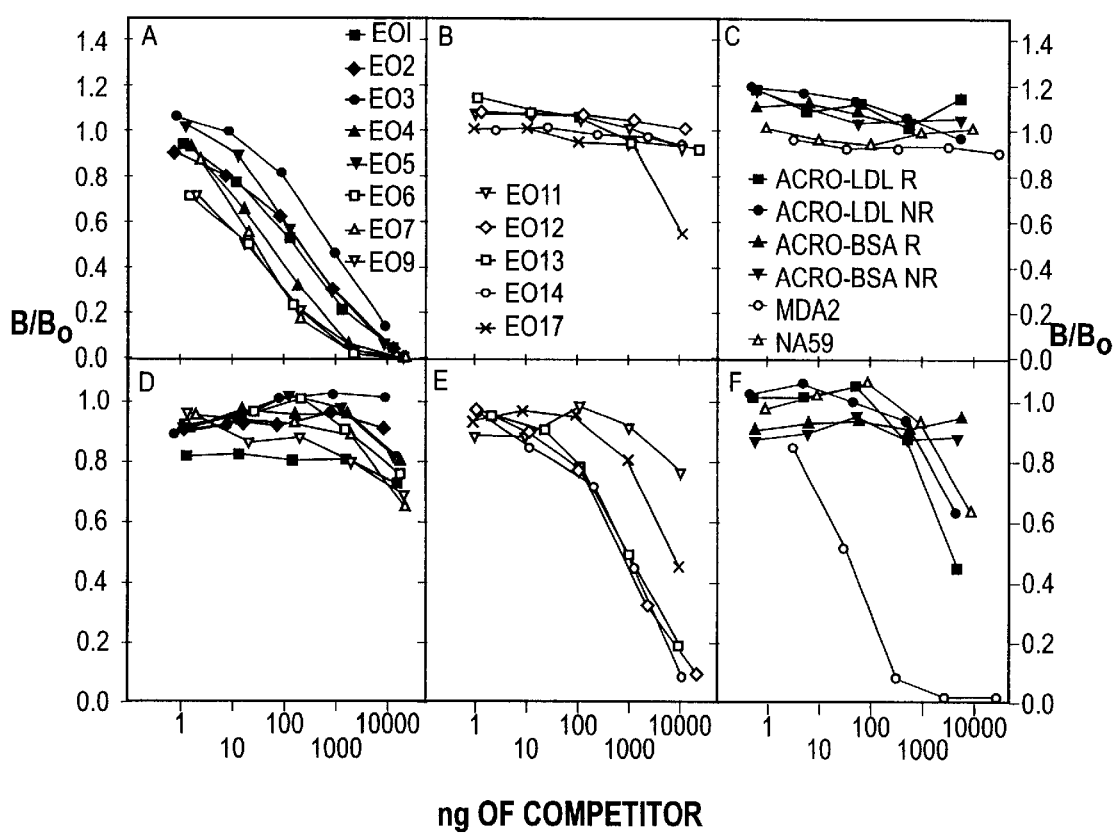
FIGS. 2(A–F) is a graph depicting the results of a competitive radioimmunoassay performed with various E0 antibodies and proteins as competitors of E04 for binding to $Cu^{2+}$-LDL. Competition by E0 antibodies originally selected for binding to $Cu^{2+}$-LDL is shown in A, that by E0 antibodies selected for binding to MDA-LDL or native LDL in B. Competition by acrolein-modified proteins and by previously generated monoclonal antibodies MDA2

Referring to FIG. 2, all antibodies originally selected for binding to Cu2+-LDL were able to effectively compete with E04 for binding to the plated antigen (FIG. 2A). The slopes of the competition curves were parallel, indicating the same relative affinity for the epitope(s) recognized. However, antibodies E01 to E09 were genuinely different and not just clones of the same antibody, as established by unique isoelectric focusing patterns. In contrast, none of the E0 antibodies originally selected for binding to MDA-LDL or native LDL competed with E04 for binding, with the exception of E013 (FIG. 2B). This is consistent with the ability of E013 to bind to Cu2+-LDL, as well as MDA-LDL. MDA2 and NA59, two previously generated monoclonal antibodies specific for MDA-lysine and 4-HNE-lysine, respectively, did not compete with E04 (FIG. 2C), demonstrating that the epitope of Cu2+-LDL recognized by E04 is different from either of these two forms of lysine modification.

In a similar manner, E014 (originally selected for binding to MDA-LDL) was characterized to further represent the E0 antibody group of E011 through E017. In this competitive RIA, MDA-LDL was plated as antigen. As shown in Table I above and FIG. 2D, none of the E0 antibodies originally selected for binding to Cu2+-LDL (E01–E09) was an effective competitor of E014. By contrast, monoclonal antibodies E012, E013, and E017, as well as E014 itself, were effective competitors. E011, the antibody originally selected for binding to native LDL competed poorly (FIG. 2E). MDA2, the induced monoclonal antibody specific for MDA-lysine, was a very efficient competitor for the binding of E014 to the plated antigen. NA59 also competed to some extent (FIG. 2F). In certain respects, the binding specificity of E014 resembles that of MDA2.

To further define the nature of the epitopes recognized by E0 antibodies, they were screened with other forms of oxidatively modified lipoproteins and proteins, based on model epitopes. These included LDL and BSA modified with (a) different concentrations of acrolein under non reducing and reducing conditions, (b) arachidonic and linoleic acid oxidation products, and (c) aldehydes such as 4-hydroxynonenal, 2-pentenal, or 2-heptenal. Preparations of MDA-LDL, in which an increasing percentage of lysine residues were modified, and LDL and HDL progressively oxidized with copper were also used in the same assay. In these experiments, a constant amount of antigen (5 g/ml) was plated, and a constant amount of the purified antibody (10 g protein/ml) was added to each well.

The entire panel of E0 antibodies was tested for binding to these and other antigens under identical conditions. The results are tabulated in Table I above and are shown in FIG. 3. Briefly, E06 (and its group mates) bound prominently to epitopes of oxidized phospholipids and oxidized phospholipid-protein adducts. E011, the antibody originally selected for its binding to native LDL, showed strong recognition of both 4-HNE-LDL and heavily modified MDA-LDL, and resembled in many aspects the monoclonal antibody NA59 previously generated by immunization with 4-HNE-LDL.

Antibodies originally selected for binding to MDA-LDL showed less uniform binding patterns. E013, E014, and E017 recognized MDA-LDL and MDA-HDL. More extensively modified forms of Cu2+-LDL were also recognized, but Cu2+-HDL was not recognized by E013 and E017 and only poorly by E014. Furthermore, E014 and E017 bound to reduced and nonreduced acrolein-modified LDL, with a preference for the nonreduced form, and to 4-HNE-LDL. However, the relative binding to these antigens, as well as the recognition of LDL modified by arachidonic or linoleic acid oxidation products was different for each antibody. E013, the antibody that had displayed an atypical recognition of Cu2+-LDL, showed particularly good binding to acrolein-LDL. E014 recognized both moderately modified MDA-LDL and acrolein-LDL, and also bound to LDL and BSA modified by fatty acid peroxidation products.

It is of interest that MDA2, which specifically binds MDA-lysine, also showed strong binding to LDL modified by arachidonic or linoleic acid oxidation products, and some binding to acrolein-modified LDL as well. Presumably, in addition to MDA, MDA-like structures, such as adducts formed with the 3-carbon aldehyde acrolein, are recognized as well, suggesting that the epitope recognized is more complex than simply MDA-lysine. None of the E0 monoclonal antibodies showed significant binding to LDL or BSA modified with 2-pentenal or 2-heptenal.

The E0 antibodies originally selected for binding to Cu2+-LDL competed poorly with E014 for binding to acrolein-LDL (FIG. 4). E0 antibodies originally selected for binding to MDA-LDL (E012, E013, and E017), which had shown binding to acrolein-modified LDL in FIG. 4 and of course E014 itself, competed effectively, indicating that they recognize the same epitope in acrolein-LDL as E014. By contrast, E011, which also bound to acrolein-LDL, did not compete with E014, indicating that this antibody recognizes a different epitope. Even though monoclonal antibody MDA2 competed for binding of E014 to MDA-LDL, it did not compete with E014 for binding to acrolein-LDL. Thus, the exact epitopes on acrolein-LDL recognized by E014 and MDA2 are different.

EXAMPLE IV

Detection of Epitopes of Oxldl on Circulating LDL by E0 Antibodies

To determine if any of the E0 series of antibodies would recognize epitopes on circulating LDL, a sensitive, double-layered sandwich chemiluminescent immunoassay was developed. In this assay, goat anti-mouse IgG-Fc-specific antiserum (GAM-IgG) was coated on microtiter wells to which monoclonal antibody MB47, which binds to apo B with high affinity, was then added as the bottom layers of the sandwich. (The GAM-IgG Fc binds MB47 so as to maximize the expression of its two binding sites.) A 1:50 dilution of plasma was then added to allow binding of LDL, the middle of the sandwich. After extensive washing, an appropriate dilution of one of the IgM antibodies against OxLDL (the E0 antibodies) was then added as the top of the sandwich, and this in turn was detected by an alkaline phosphatase-labeled goat anti-IgM antibody. Non specific murine IgM were used in place of E0 antibodies as a control.

As shown in FIG. 5, antibodies E06 and E014 clearly recognized three to four times the amount of epitope on these LDL as did the other monoclonal antibodies or non-specific IgM controls. In separate experiments, the data were confirmed by "inverting the sandwich." The E0 antibodies were plated, plasma added, and then MB47 (directly labeled with alkaline phosphatase) was used to document that LDL was bound by the E0 antibodies. Again, E06 and E014 bound significantly more LDL than did the other E0 antibodies.

In separate and parallel wells, an alkaline phosphatase-labeled MB24, another apo B-specific monoclonal, which recognizes a distinct and noncompeting epitope on apo B was used to verify that equal amounts of LDL were bound by MB47 from each of the plasmas added; e.g., that under the assay conditions used, the amount of plasma LDL added saturates the capacity of MB47 binding.

Binding curves from pooled sera for IgM E0 antibodies are shown in FIG. 5. The original screening antigens (Cu2+-LDL, MDA-LDL, 4-HNE-LDL) were also used in the same assays for comparison. In sera from apo E-deficient mice, the titer of IgM E0 antibodies to MDA-LDL was the highest, followed by the titers to Cu2+-LDL and 4-HNE-LDL (FIG. 5A). Autoantibody titers to nonreduced or reduced acrolein-LDL and AOP-LDL were comparable to those against Cu2+-LDL and 4-HNE-LDL (FIG. 5 B). Somewhat lower titers were also present against LOP-LDL. In contrast, sera from C57BL/6 mice contained measurable autoantibody titers only to MDA-LDL (FIG. 5 C). Results for IgG E0 antibodies were essentially identical to those obtained for IgM E0 antibodies.

Sera from six human subjects were also screened for IgG and IgM having binding specificities comparable to E0 antibodies to acrolein-modified LDL, and, for reasons of comparison, for E0 antibodies to MDA-LDL and native LDL. All human sera had E0 antibodies to acrolein-LDL comparable to those against MDA-LDL (titers between 1,000 and 10,000). Titers of E0 antibodies to both MDA-LDL and acrolein-LDL were highest in two subjects with clinical manifestations of atherosclerosis, whereas the lowest titer was found in a patient with cholesterol emboli syndrome, which occurred after aortic balloon counterpulsation therapy for shock. This suggests that intravascular dissemination of plaque material may have "absorbed" most of the circulating antibodies in the patient with the emboli.

EXAMPLE V

Binding of Atherosclerotic Lesions by E0 Antibodies

Selected E0 antibodies were used to immunostain atherosclerotic lesions of LDL receptor-deficient rabbits, balloon-catheterized, cholesterol-fed New Zealand white (NZW) rabbits, and human brain arteries obtained at autopsy. For comparison, MDA2 antibody (specific for MDA-lysine) and NA59 antibody (specific for 4-HNE-lysine) were used. Smooth muscle cells in human lesions were discriminated from plaque by immunocytochemistry with HHF35, a monoclonal antibody recognizing alpha and gamma actin (Enzo Diagnostics, Inc., Farmingdale, N.Y.). Macrophage-derived cells in human lesions were stained with HAM56 (Enzo Diagnostics). Tissues were fixed in formal sucrose (4% paraformaldehyde, 5% sucrose) (rabbit arteries) or 10% formaldehyde (human arteries) and paraffin-embedded. Serial sections (8 m thick) were rehydrated and immun-ostained using an avidin-biotin-alkaline phosphatase system (Vector Laboratories, Inc., Burlingame, Calif.).

Primary antibodies bound to the tissue were detected with biotinylated anti-mouse immunoglobulin serum (Vector Laboratories, Inc.). Control slides were incubated without primary antibody. Differences in specificity between the cloned E0 antibodies established by binding and competition assays indicates that these antibodies see different parts of the same structure (or of immunologically related structures). To confirm this hypothesis and the in vivo occurrence of the epitopes recognized, immunocytochemistry with the entire panel of E0 monoclonal antibodies was performed on serial sections of atherosclerotic lesions of various stages and of different composition.

Atherosclerotic lesions were studied in arteries from LDL receptor-deficient rabbits, NZW rabbits in which lesion formation had been induced by balloon catheterization and feeding of a cholesterol-rich diet, and in brain arteries from human subjects obtained at autopsy. In general, in early atherosclerotic lesions from both cholesterol-fed NZW and LDL receptor-deficient rabbits, staining was predominantly foam-cell associated, although diffuse extracellular staining was also observed in some areas. More advanced lesions showed "oxidation-specific" epitopes in the shoulder regions and in the cap, as well as diffuse staining in the necrotic core. Normal arteries showed no intimal staining with the E0 antibodies, and control sections in which the primary antibody was omitted were devoid of any staining.

In most of the early and transitional lesions examined, the distribution of immunostaining obtained with natural monoclonal antibodies of different specificity was very similar. However, in some very advanced lesions from LDL receptor-deficient rabbits, significant differences were found even between antibodies originally selected for binding to the same epitope. For example, an area adjacent to the internal elastic lamina in a very advanced lesion was rich in epitopes recognized by E04 and most other E0 antibodies, but not by E017.

Immunocytochemistry was therefore extended to very advanced atherosclerotic lesions found in human brain arteries. The human specimens were obtained postmortem and may have undergone some ex vivo oxidation. These human arteries were used to compare the natural and induced monoclonal antibodies to OxLDL.

Some of the E0 antibodies showed distinct staining patterns. In general, staining was most intense in a necrotic area, although diffuse staining was found throughout the core region. Macrophage- and smooth muscle cell-derived foam cells in the shoulder area and cap also stained. Antibody E04 yielded virtually identical staining patterns as E01 and E03. Staining with E06 was also very similar, with both cellular and extracellular staining, in particular in the core. In contrast, E011 recognized epitopes almost exclusively in the core, and showed almost no cellular staining in the cap. E014 also showed a unique staining pattern in this particular lesion, and recognized epitopes almost exclusively found in the cell-rich shoulder area and cap. E017 showed relatively weak staining in both cell-rich and necrotic areas, but lacked the predominance of the staining in the necrotic core.

Surprisingly, immunostaining with MDA-2, a monoclonal antibody generated with MDA-LDL, was more similar to that obtained with E0 antibodies originally selected for binding to Cu2+-LDL than to that of E014 and E017, originally selected for binding to MDA-LDL. These results not only confirm the differences in specificity between the E0 antibodies, but also suggest that specific epitopes may be formed during different stages of lesion development and/or at certain sites within lesions, or that conservation of these epitopes occurs differentially at different sites. Again, control sections stained without primary antibody were devoid of any staining.

EXAMPLE VI

Monitoring of Lipoprotein Oxidation in Primates

As models of susceptibility to atheroma formation, groups of primates were raised to an age of 6–8 years with an exclusive diet of cholesterol-rich foods. Blood lipoproteins in such animals have undergone a degree of hydroperoxidation. Copper-induced lipoprotein oxidation is dependent on the presence of lipid hydroperoxides in the lipoprotein substrate, and develops in proportion to the degree of pre-existing hydroperoxides. Thus, a change in the numbers of oxidation-specific epitopes on blood lipoproteins is a marker for progression or regression of lipoprotein hydroperoxidation as a precursor to atheroma formation.

One group of the high cholesterol-fed animals was treated by feeding a low cholesterol diet for 5 months. Efficacy of the treatment was evaluated by applying the double capture immunoassay to plasma LDL obtained from each animal under oxidation-protective conditions, as described. Each sample was treated with copper for two hours. Expression of oxidation-specific epitopes on LDL were measured before and after copper oxidant treatment of each sample. Data were expressed as the ratio of oxidation-specific epitope expression per LDL particle after copper oxidation divided by oxidation-specific epitope expression per LDL particle before copper oxidation. In this experiment, the E0 antibody was E06; therefore, oxidation-specific epitopes measured were those bound by E06.

As shown in FIG. 6, there was a marked decrease in the number of oxidation-specific epitopes per LDL particle in the treated animals as compared to the untreated animals, indicating a reduction in the rate of lipoprotein oxidation had occurred in treated animals during the five month treatment period. This same assay method can be applied to monitor the efficacy of treatment, as well as progression or recurrence of disease, in other species with LDL having cross-reactivity with E0 antibodies (including humans).

EXAMPLE VII

E0 Antibody Inhibition of OxLDL Binding by Macrophages

To confirm the capacity of E0 antibodies to inhibit binding of OxLDL to macrophage scavenger receptors (the precursor to foam cell formation), mouse peritoneal macrophages were prepared by saline lavage of the peritoneal cavity of anesthetized mice and maintained in cell culture overnight. $^{125}$I-labeled copper oxidized LDL was added to microtiter plate wells (2 µg/0.5 mL per well) containing the cultured macrophages. The plates were chilled to 4° C. to prevent internalization and degradation of the label by the macrophages. 50 µg of various LDL antigens known to be taken up by macrophages (including copper oxidized LDL) were added to some of the wells as binding competitors, while 50 µg of different E0 antibodies were added to other wells.

The amount of labeled OxLDL bound to the surface of the cells was determined by first removing the media containing the added OxLDL, extensively washing the plates then solubilizing the plated cells. Aliquots of the cells were counted in a gamma counter.

As shown in FIG. 7, in the presence of copper oxidized LDL as a competitor, binding of the labeled OxLDL antigen decreased to less than 10% of the control value (binding in the absence of competition; 100% in the FIGURE), demonstrating that at least 90% of the binding in this assay was antigen-specific. For comparison, no competition occurred in the presence of added MDA-LDL or Acro LDL.

In the presence of E01, E03, E04, E06, E07 or E09, macrophage binding of OxLDL was inhibited to between 50% and 80% of the control binding value, depending on the antibody used. In contrast, little or no inhibition was obtained using antibodies not specific for copper-oxidation LDL epitopes (E011, E017 and MDA2).

Similar results are obtained for inhibition of uptake and degradation of OxLDL by macrophages (data not shown). The inhibitory effect of the E0 antibodies is essentially dose dependent, with degradation inhibition of up to 80%–90% being achieved at saturation levels.

The invention having been fully described, modifications to the methods and reagents of the invention may be apparent to those of ordinary skill in the art. All such modifications are within the scope of the invention.

The invention claimed is:

1. A method for detecting oxidation-specific epitopes on lipoprotein present in the blood, arterial or vascular tissue of a host, the method comprising:
   a) contacting the lipoprotein with a detectably labeled monoclonal antibody having binding specificity for oxidation-specific epitopes on oxidatively modified lipoprotein in atherosclerotic lesions and blood, which monoclonal antibody is produced in apolipoprotein deficient mice ("E0 antibody"); and,
   b) determining whether the E0 antibody binds the lipoprotein, wherein E0 antibody binding is indicative of the presence of lipoprotein having oxidation-specific epitopes thereon.

2. The method according to claim 1, further comprising the step of c) measuring the number of oxidation-specific epitopes bound by the E0 antibody.

3. The method according to claim 1, wherein step b) is performed in a sandwich immunoassay comprising the steps of:
   i) adding a sample of lipoprotein isolated from host blood, arterial or vascular tissue to a substrate coated with with a monoclonal antibody having binding specificity for a lipoprotein;
   ii) adding a known quantity of the E0 antibody to the substrate; and,
   iii) detecting binding of the lipoprotein by the E0 antibody.

4. The method according to claim 3, wherein the monoclonal antibody of step i) is plated in a quantity sufficient to bind all of the lipoprotein in the sample, and step iii) is performed by calculating the ratio of lipoprotein particles bound by the monoclonal antibody to the extent of binding of the lipoprotein by the E0 antibody.

5. The method according to claim 3, wherein the sample of lipoprotein is protected from ex vivo oxidation through isolation in the presence of an antioxidant.

6. The method according to claim 5, wherein the antioxidant is plasma.

7. The method according to claim 1, wherein the lipoprotein is LDL.

8. The method according to claim 1, wherein the E0 antibody is detectably labeled with a molecule detectable in a chemiluminescent assay.

9. The method according to claim 1, wherein the E0 antibody is detectably labeled with a radioisotope or magnetic particle.

10. The method according to claim 9, wherein the oxidation-specific epitopes are detected in vivo.

11. The method according to claim 3, wherein the monoclonal antibody of step i) is MB47 or MB24.

12. A method for screening antibodies and blood samples for, respectively, binding affinity for oxidation epitopes on lipoprotein and susceptibility to lipoprotein oxidation, the method comprising:
    a) contacting a sample of lipoprotein obtained from the host with a pro-oxidant;
    b) contacting the lipoprotein with a detectably labeled monoclonal antibody having binding specificity for oxidation-specific epitopes on oxidatively modified lipoprotein in atherosclerotic lesions and blood, which monoclonal antibody is produced in apolipoprotein deficient mice ("E0 antibody"); and,
    c) determining whether the E0 antibody binds the lipoprotein, wherein binding indicates that the antibody has binding affinity for oxidation epitopes induced by the pro-oxidant and the lipoprotein is susceptible to oxidation.

13. The method according to claim 12, further comprising the step of d) measuring the number of oxidation-specific epitopes bound by the E0 antibody.

14. The method according to claim 12, further comprising step (a), wherein the sample of lipoprotein is protected from ex vivo oxidation while being obtained from the host through treatment of the lipoprotein with an antioxidant.

15. The method according to claim 14, wherein the antioxidant is plasma.

16. The method according to claim 12, wherein the lipoprotein is LDL.

17. A method for monitoring lipoprotein oxidation in a host, the method comprising comparing the measurement obtained according to the methods of claim 2 to subsequent measurements obtained according to the methods of claim 2, wherein an increase in E0 antibody binding indicates that the lipoprotein is becoming increasingly oxidized and no change in E0 antibody binding indicates that further oxidation of the lipoprotein has not occurred.

18. A method for identifying inhibitors of foam cell formation in a host, the method comprising:
    a) contacting a sample of oxidized lipoprotein with cells including macrophages;
    b) contacting the sample of oxidized lipoprotein with a detectably labeled monoclonal antibody having binding specificity for oxidation-specific epitopes on oxidatively modified lipoprotein in atherosclerotic lesions and blood, which monoclonal antibody is produced in apolipoprotein deficient mice ("E0 antibody");
    c) contacting the sample of oxidized lipoprotein with a candidate inhibitor; and,
    d) determining wherein the candidate inhibitor competes with the E0 antibody to block binding of the oxidized lipoprotein to the macrophages, wherein E0 antibody binding is indicative of the presence of lipoprotein having oxidation-specific epitopes thereon.

* * * * *